(12) United States Patent
Kreidler et al.

(10) Patent No.: US 9,127,030 B2
(45) Date of Patent: Sep. 8, 2015

(54) METHOD FOR THE PREPARATION OF BIPHEPHOS

(75) Inventors: Burkard Kreidler, Essen (DE); Dirk Fridag, Haltern am See (DE); Bernhard Schemmer, Haltern am See (DE); Bjoern Wechsler, Borken (DE); Andrea Christiansen, Neu-Ulm (DE); Doris Neumann, Offenbach a. M. (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 13/979,548

(22) PCT Filed: Dec. 22, 2011

(86) PCT No.: PCT/EP2011/073762
§ 371 (c)(1),
(2), (4) Date: Aug. 14, 2013

(87) PCT Pub. No.: WO2012/095253
PCT Pub. Date: Jul. 19, 2012

(65) Prior Publication Data
US 2013/0324756 A1 Dec. 5, 2013

(30) Foreign Application Priority Data
Jan. 13, 2011 (DE) .......................... 10 2011 002 639

(51) Int. Cl.
*C07F 9/6571* (2006.01)
*C07F 9/6574* (2006.01)
(52) U.S. Cl.
CPC ........... *C07F 9/6571* (2013.01); *C07F 9/65746* (2013.01)
(58) Field of Classification Search
CPC .................................................... C07F 9/6571
See application file for complete search history.

(56) References Cited

U.S. PATENT DOCUMENTS

| 7,767,861 B2 * | 8/2010 | Ortmann et al. ............. 568/10 |
| 2007/0112219 A1 | 5/2007 | Ortmann et al. |
| 2011/0201837 A1 | 8/2011 | Fridag et al. |
| 2011/0207966 A1 | 8/2011 | Fridag et al. |

FOREIGN PATENT DOCUMENTS

| WO | 2005 063776 | 7/2005 |
| WO | 2010/052091 | 5/2010 |

* cited by examiner

*Primary Examiner* — Sun Jae Yoo
(74) *Attorney, Agent, or Firm* — Oblon, McClelland, Maier & Neustadt, L.L.P.

(57) ABSTRACT

The invention relates to a process for producing 6,6'-[(3,3'-di-tert-butyl-5,5'-dimethoxy-1,1'-biphenyl-2,2'diyl)bis(oxy)]bis(dibenzo[d,f][1,3,2]dioxaphosphepine), abbreviated to biphephos (see formula 1), with low chlorine content.

Formula 1

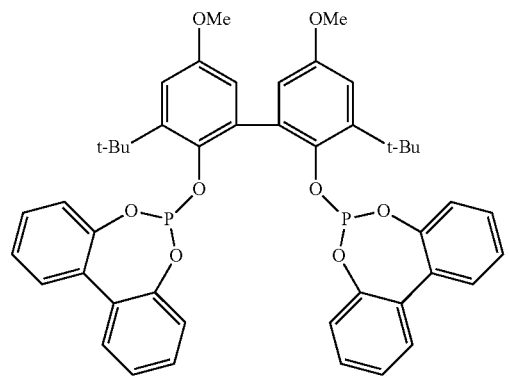

19 Claims, No Drawings

METHOD FOR THE PREPARATION OF BIPHEPHOS

CROSS REFERENCE TO RELATED APPLICATIONS

The present application is a 35 U.S.C. §371 national stage patent application of international patent application PCT/EP2011/073762, filed on Dec. 22, 2011, published as WO 2012/095253 on Jul. 19, 2012, the text of which is incorporated by reference, and claims the benefit of the filing date of German Patent Application No. 10 2011 002 639.8, filed on Jan. 13, 2011, the text of which is also incorporated by reference.

The invention relates to a process for producing 6,6'-[(3,3'-di-tert-butyl-5,5'-dimethoxy-1,1'-biphenyl-2,2'diyl)bis(oxy)]bis(dibenzo[d,f][1,3,2]-dioxaphosphepine), abbreviated to biphephos (see formula 1), with low chlorine content.

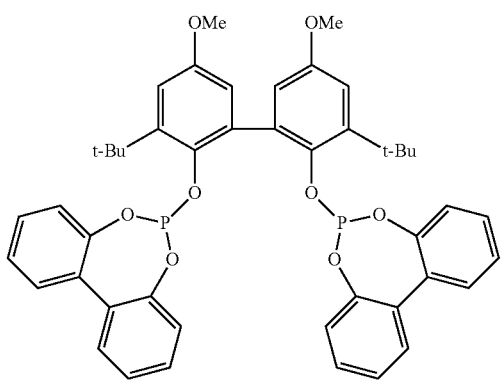

Formula 1

Biphephos is a ligand which has become widely used in transition-metal-catalyzed reactions. By way of example, biphephos is used in transition-metal-catalyzed hydroaminomethylation (E. Petricci, A. Mann, J. Salvadori, M. Taddei, Tetrahedron Letters 2007, 48, 8501-8504), hydrocyanation (U.S. Pat. No. 5,449,807), hydroformylation (U.S. Pat. No. 4,769,498, CN1986055), isomerisation (U.S. Pat. No. 5,440,067) and cyclohydrocarbonylation (U.S. Pat. No. 5,962,744) of olefins.

Biphephos is usually produced in 3 synthetic steps from commercially available starting materials: the main skeleton is produced by reacting 3-tert-butyl-4-hydroxyanisole oxidatively to give the biaryl compound 3,3'-tert-butyl-2,2'-dihydroxy-5,5'-dimethoxybiphenyl. To produce the side lobes, phosphorus trichloride is reacted with 2,2'-dihydroxybiphenyl to form 6-chlorodibenzo[d,f][1,3,2]-dioxaphosphepine (see formula 2). Finally, the reaction products from both steps mentioned are condensed with one another in the presence of a base to give biphephos.

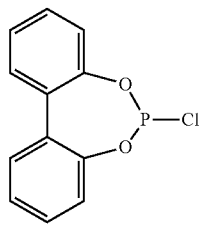

Formula 2

Biphephos is most widely used in the hydroformylation of propene to give n-butyraldehyde. Here, propene is reacted with hydrogen and carbon monoxide in the presence of rhodium as catalyst metal and biphephos as ligand. Pressure reactors made of steel are generally used for the reaction. The said reactors are very easily damaged by traces of hydrogen chloride which can form from chloride ions in the presence of transition metals and of elemental hydrogen. Chloride ions bring the threat of stress cracking corrosion, which in less severe cases can cause premature shutdown and overhaul of the reactor, but in the most severe cases can cause the reactor to burst.

The introduction of chloride ions via the olefin or the synthesis gas can be suppressed by using steps known to the person skilled in the art (e.g. absorber beds). When the catalyst metal is added it is advisable to use a chlorine-free species, such as rhodium methylhexanoate or $Rh(acac)(CO)_2$.

Since biphephos is fundamentally formed from $PCl_3$, particular efforts have to be made if chlorine content in the resultant biphephos is to be minimized. In the case of hydroformylation of propene, relatively high chlorine contents are less critical, since only very little degradation of biphephos takes place at the temperatures required for that process. However, hydroformylation of higher olefins generally requires higher temperatures, and these bring about accelerated degradation of biphephos. This means that fresh biphephos has to be added subsequently to compensate for the constant degradation of biphephos in any continuously operating hydroformylation process. If biphephos comprises traces of chloride, this then means that chloride gradually accumulates within the reactor, so that there is practically no discharge of chloride out of the reactor. The rising chloride content therefore considerably increases the risk of stress cracking corrosion.

It is therefore important to develop a biphephos production process which provides biphephos with low chloride content. Chloride content can be determined by a simple analytical method, for example via aqueous titration. A more widely used approach determines total chlorine content, which comprises not only the chlorides but also forms of bound chlorine. Another advantage of decisions based on total chlorine content is that other forms of bound chlorine could possibly damage the reactor. However, chloride content is still the decisive factor when threshold values for total chlorine are set. 5000 ppm of total chlorine can be considered to be a highest threshold value, and it is preferable that the biphephos produced should comprise less than 4000 ppm of total chlorine, particularly less than 3000 ppm. A process developed in parallel permits further reduction of chlorine content.

A suitable method for determining total chlorine content is Wickbold combustion; with specimen preparation to DIN 51408 and measurement by ion chromatography to DIN EN ISO 10304.

In J. Am. Chem. Soc. 1993, 115, 2066-2068, the hydrogen chloride gas produced during the reaction was scavenged by triethylamine. The reaction took place in toluene, in which not only biphephos but also the coupling product triethylamine hydrochloride precipitated. Cooling to −40° C. was required. The hydrochloride produced was removed through washing with water, filtration and recrystallization from acetonitrile. Washing with water produces an acidic solution of amine hydrochloride which requires specific filter equipment, for example made of corrosion-resistant Hastelloy. Biphephos moreover only has restricted stability in water and can hydrolyze, and this explains the low final yield of only 64%. As batch size increases, time in contact with water increases, and the extent of hydrolysis is likely to increase. Aqueous work-up is therefore not advisable for industrial batch sizes.

In WO2005/063776, the object was achieved in that the amine base used comprised a polymeric ion exchanger. The amine hydrochloride in that document is polymeric and can be obtained by filtration. The yield was 50%. The loaded ion exchanger then either has to be reactivated in a separate process step or requires disposal.

In Organometallics 1996, 15, 835-847, Rooy et al. describe the synthesis of biphephos in tetrahydrofuran as solvent in the presence of pyridine as base. The only reaction temperature stated, −50° C., is not achievable in industry unless very high costs are incurred for apparatus and for energy. However, the advantage of the said process is that the amine hydrochloride coupling product substantially precipitates and can be removed through filtration from the biphephos-containing solution. A large amount of energy then has to be used to draw off the solvent. The product is precipitated by adding acetonitrile and is again filtered. The yield is considerably better than in the two above processes, being 79%. Disadvantages of this process are: a) extreme low temperatures of −50° C. which cannot be achieved unless considerable cost is incurred for energy and for apparatus, b) distillation of THF and pyridine, which requires energy, the appropriate apparatus, and also time, and c) double filtration, which incurs high operating cost and consumes plant capacity.

Some studies carried out by the applicant moreover revealed that temperatures above −50° C. cause increased formation of compounds isomeric with biphephos, in particular an isomer of the formula 3.

Formula 3

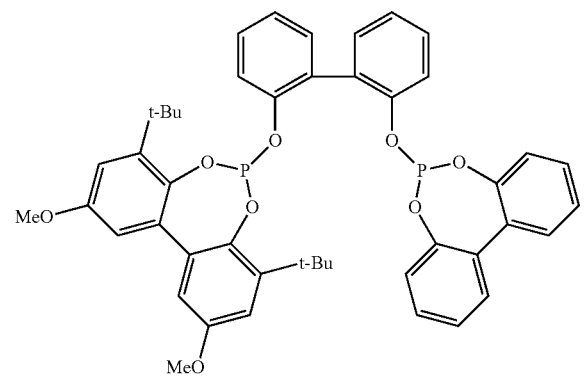

EP0577042 improves the said process, the reaction being carried out at −5° C. in toluene. According to EP0577042, pyridine hydrochloride precipitates here, but biphephos remains in solution. Toluene was then removed by distillation, and biphephos was precipitated using acetonitrile, and the solvent was removed by distillation. Here again, double filtration is required. Some investigations moreover revealed that this method gives only very small yields in the single-digit-percent region, because most of the biphephos precipitates in toluene and is removed by filtration together with pyridine hydrochloride and discarded.

It was then an object of the present invention to develop a low-cost synthetic method which is easy to implement on an industrial scale for biphephos and which gives biphephos with low total chlorine content of less than 5000 ppm and in high yield, and which does not require aqueous work-up.

The said object is achieved through a process for producing biphephos by reaction of 3,3'-tert-butyl-2,2'-dihydroxy-5,5'-dinnethoxybiphenyl with 6-chlorodibenzo[d,f][1,3,2]dioxaphosphepine, characterized in that the reaction takes place in a solvent mixture comprising acetonitrile.

When a "solvent mixture" is mentioned here, this means not only a mixture of two or more different solvents, where one of these is acetonitrile, but also pure acetonitrile. In one preferred embodiment of the process according to the invention, the solvent mixture comprises at least 40% by weight, preferably at least 50% by weight, more preferably at least 60% by weight, still more preferably at least 70% by weight, most preferably 80% by weight, of acetonitrile, based on the total amount of solvent. The reaction can also take place in pure acetonitrile (solvent comprising from 95 to 100% by weight of acetonitrile content).

The solvent mixture can comprise up to 60% by weight, preferably up to 50% by weight, more preferably up to 40% by weight, still more preferably up to 30% by weight, most preferably up to 20% by weight, based on the total amount of solvent, of other solvents. Other solvents that can be selected with preference are those from the group consisting of toluene, ortho-xylene, n-heptane, ethyl acetate, propylene carbonate and mixtures thereof, preference being given here to toluene, ortho-xylene, n-heptane, ethyl acetate and mixtures thereof.

In one preferred embodiment of the process according to the invention, the reaction takes place in the presence of a base, preferably in the presence of pyridine or n-butyldimethylamine.

"Solvents" are intended here to be only the substances actually used as solvents, i.e. the constituents which are liquid at 23° C. in the reaction mixture and which do not themselves undergo any chemical reaction with the starting materials 3,3'-tert-butyl-2,2'-dihydroxy-5,5'-dimethoxybiphenyl and 6-chlorodibenzo[d,f][1,3,2]-dioxaphosphepine or with the product biphephos. Among the solvents are therefore by way of example in particular acetonitrile, toluene, ortho-xylene, n-heptane, ethyl acetate and propylene carbonate. In contrast, pyridine, triethylamine and similar compounds having a basic function are not intended to be regarded as solvents.

It has been found particularly advantageous to produce biphephos as described above, in particular in the presence of pyridine as base and in acetonitrile as solvent. When this combination is used it is possible to use simple brine cooling, i.e. above the crystallization temperature of a eutectic mixture of water and sodium chloride, to react 6-chlorodibenzo[d,f][1,3,2]-dioxaphosphepine 2 with 3,3'-tert-butyl-2,2'-dihydroxy-5,5'-dimethoxybiphenyl to form biphephos and then to obtain the product by filtration. In order to increase shelf life, it is also optionally possible to wash the product with an inert solvent, e.g. n-heptane. This typically gives a yield of more than 80% of the resultant product, which comprises less than 5000 ppm of chloride, preferably less than 4000 ppm, and particularly preferably less than 3000 ppm.

When pyridine is used, temperatures can be considerably higher than is the case with triethylamine as in the method used by Rooy et al. (vide supra). Pyridine hydrochloride moreover has excellent solubility in acetonitrile, which is used as solvent for the synthesis, and remains in the solvent, whereas biphephos is insoluble in acetonitrile and therefore precipitates. It is therefore possible to obtain biphephos with total chlorine content markedly less than 5000 ppm, preferably less than 4000 ppm, and particularly preferably less than 3000 ppm, based on the biphephos after isolation and drying. Sample preparation for determination of total chlorine content by the Wickbold combustion method is to DIN 51408, and measurement is to DIN EN ISO 10304 (by ion chromatography).

The reaction can advantageously be conducted in the temperature range from above the crystallization temperature of a eutectic mixture of water and sodium chloride up to 10° C. In one preferred embodiment of the process according to the invention the reaction takes place in the temperature range from above −10° C. to 5° C.

When the reaction is complete, the resultant solid can be isolated. The typical method used for this is filtration and, optionally, drying of the solid after filtration. It is preferable that—before optional drying of the solid obtained by filtration—it is re-slurried in a solvent suitable for this purpose, optionally repeatedly in the same solvent or repeatedly in various suitable solvents, and subjected to filtration. Suitable solvents for the slurrying process are acetonitrile, propylene carbonate, n-heptane and hydrocarbons. Among the hydrocarbons, preference is given to the C5-C12-hydrocarbons and (cyclo)alkanes.

The biphephos can be recrystallized for further purification. The method for achieving this in one preferred embodiment of the process according to the invention, after reaction of the starting materials is complete and optionally after isolation of the solid product, the said solid composed mainly of biphephos is dissolved, preferably with heating, in an acetonitrile-free solvent or solvent mixture, insoluble constituents are removed by filtration, preferably at a temperature up to 130° C., and the biphephos is precipitated or crystallized through cooling of the solvent or solvent mixture. The biphephos can then be isolated, preferably being obtained by filtration and, optionally, drying of the pure product obtained by filtration. A typical method of achieving solution of the solid, composed mainly of biphephos, in an acetonitrile-free solvent or solvent mixture is heating of the solvent or solvent mixture. Cooling to room temperature or a lower temperature can then be carried out.

When the process described above is compared with the variants described in the prior art, it incurs less cost for apparatus and energy and is less time-consuming. The advantages of the process are:

The reaction can be conducted with normal brine cooling, high yields above 80% can be achieved,
biphephos is obtained with chlorine content less than 3000 ppm without recrystallization, and
there is no aqueous work-up.

The present invention further provides the use of acetonitrile as solvent or constituent of a solvent mixture in a process for producing biphephos. In one preferred embodiment of the use according to the invention, 3,3'-tert-butyl-2,2'-dihydroxy-5,5'-dimethoxybiphenyl is reacted with 6-chlorodibenzo[d,f][1,3,2]dioxaphosphepine in the solvent acetonitrile or the solvent mixture comprising acetonitrile.

EXAMPLE

Example 1

Production of Biphephos 17.5 g (0.063 mol) of phosphorochloridite 2, produced according to DE-A102008043584, are used as initial charge in 110 mL of acetonitrile (Fluka) in a 250 mL Schlenk flask in a glove box. 10.4 g (0.028 mol) of 3,3'-tert-butyl-2,2'-dihydroxy-5,5'-dimethoxybiphenyl were also prepared according to EP35965. This was dissolved in 17 ml (16.4 g, 0.204 mol) of pyridine and charged to a 100 mL dropping funnel. This was placed on the Schlenk flask. The apparatus was removed from the glove box, and the Schlenk flask was cooled to −10° C. The biphenol/pyridine solution was then metered dropwise into the mixture within a period of 2.5 h, with vigorous stirring, whereupon a solid precipitated. Once addition was complete, stirring of the mixture was continued overnight at −10° C. The solid was then obtained by filtration by way of a G3 frit under inert gas. The solid was then slurried under inert gas on the frit in 30 ml of acetonitrile, and the mixture was again filtered. The colourless solid was dried at 10^-1 mbar for 16 hours, and then analyzed. The amount of biphephos obtained was 19.92 g (87.3% of theory). The total chlorine content of this was 2500 ppm (±100 ppm) (analysis method: Wickbold combustion to DIN 51408 and DIN EN ISO 10304).

Example 2

Production of Biphephos 121 g of phosphorochloridite 2, 80% in toluene, are dissolved in 530 g of acetonitrile and cooled to −5° C. 63 g of 3,3'-tert-butyl-2,2'-dihydroxy-5,5'-dimethoxybiphenyl were dissolved in 101 g of pyridine and slowly metered into the phosphorochloridite solution, while the reaction solution was constantly cooled to −5° C. Once the addition was complete, stirring was continued for 2 h.

The precipitated product was obtained by way of a suction filter and washed first with 80 mL of acetonitrile and then with 100 mL of n-heptane, and dried in a vacuum drying cabinet. This gave 114 g (83% of theory) of biphephos with total chlorine content 1500 ppm (±100 ppm) (analysis method: Wickbold combustion to DIN 51408 and DIN EN ISO 10304).

The invention claimed is:

1. A process for producing biphephos, the process comprising:
reacting 3,3'-tert-butyl-2,2'-dihydroxy-5,5' dimethoxybiphenyl with 6-chlorodibenzo[d,f][1,3,2]dioxaphosphepine in the presence of a base and a solvent mixture comprising acetonitrile;
wherein:
the reaction provides a biphephos product having a total chlorine content of less than 5000 ppm; and
the reaction provides a biphephos yield of greater than 80%.

2. The process according to claim 1, wherein the solvent mixture comprises at least 40% by weight of acetonitrile.

3. The process according to claim 1, wherein the solvent mixture further comprises up to 60% by weight of at least one solvent different from acetonitrile.

4. The process according to claim 3, wherein the at least one solvent different from acetonitrile is selected from the group consisting of toluene, ortho-xylene, n-heptane, ethyl acetate, and propylene carbonate.

5. The process according to claim 1, wherein the reacting takes place in a temperature range from above a crystallization temperature of a eutectic mixture of water and sodium chloride up to +10° C.

6. The process according to claim 5, wherein the reacting takes place in a temperature range from above −10° C. to +5° C.

7. The process according to claim 1, further comprising:
isolating a resultant solid after the reacting.

8. The process according to claim 1, further comprising, after the reacting and optional isolating:
dissolving a solid mainly comprising biphephos in an acetonitrile-free solvent or solvent mixture,
removing insoluble constituents by filtration,
crystallizing or precipitating biphephos via cooling of the acetonitrile-free solvent or solvent mixture, and
isolating the biphephos.

9. The process according to claim 2, wherein the solvent mixture comprises at least 80% by weight of acetonitrile.

10. The process according to claim 3, wherein the solvent mixture further comprises up to 20% by weight of the at least one solvent different from acetonitrile.

11. The process according to claim 10, wherein the at least one solvent different from acetonitrile is selected from the group consisting of toluene, ortho-xylene, n-heptane, ethyl acetate, and propylene carbonate.

12. The process according to claim 1, wherein the base is pyridine.

13. The process according to claim 8, wherein the isolating the solid comprises filtering.

14. The process according to claim 13, further comprising:
drying the solid.

15. The process according to claim 10, wherein isolating the biphephos comprises filtering.

16. The process according to claim 15, further comprising drying the biphephos obtained by filtration.

17. The process according to claim 13, further comprising:
re-slurrying the solid obtained by filtration in a solvent.

18. The process according to claim 17, further comprising:
repeating the re-slurrying in the solvent or a different solvent.

19. The process according to claim 17, further comprising:
drying the solid obtained by filtration.

* * * * *